US011883309B2

(12) United States Patent
Malek

(10) Patent No.: US 11,883,309 B2
(45) Date of Patent: Jan. 30, 2024

(54) DIRECTIONAL STENT FOR ACCESSING EXTRAVASCULAR SPACES

(71) Applicant: CEREVASC, INC., Auburndale, MA (US)

(72) Inventor: Adel M. Malek, Weston, MA (US)

(73) Assignee: CereVasc, Inc., Auburndale, MA (US)

( * ) Notice: Subject to any disclaimer, the term of this patent is extended or adjusted under 35 U.S.C. 154(b) by 752 days.

(21) Appl. No.: 16/888,455

(22) Filed: May 29, 2020

(65) Prior Publication Data

US 2020/0375766 A1 Dec. 3, 2020

Related U.S. Application Data

(60) Provisional application No. 62/854,684, filed on May 30, 2019.

(51) Int. Cl.
*A61F 2/856* (2013.01)
*A61B 17/34* (2006.01)
*A61B 17/00* (2006.01)

(52) U.S. Cl.
CPC .......... *A61F 2/856* (2013.01); *A61B 17/3423* (2013.01); *A61B 2017/00292* (2013.01); *A61B 2017/3425* (2013.01); *A61F 2250/0098* (2013.01)

(58) Field of Classification Search
CPC .. A61F 2/856; A61F 2/90; A61F 2/962; A61F 2250/0098; A61F 2002/9528; A61B 17/3423; A61B 2217/005; A61B 2090/101; A61B 2090/3735; A61B 2090/376; A61B 2090/378; A61B 10/0241; A61B 10/06; A61B 2017/00292; A61B 2017/3425; A61B 2017/0061; A61B 2017/22069; A61B 2017/22077; A61B 2017/22084; A61B 2017/22095; A61B 17/22; A61B 17/3468; A61B 17/3478

See application file for complete search history.

(56) References Cited

U.S. PATENT DOCUMENTS

| 10,258,284 | B1 | 4/2019 | Malek et al. |
| 2012/0053485 | A1* | 3/2012 | Bloom .............. A61M 25/1002 600/104 |
| 2016/0324670 | A1* | 11/2016 | Yamaguchi ............... A61F 2/07 |
| 2019/0307403 | A1 | 10/2019 | Malek et al. |
| 2020/0375723 | A1* | 12/2020 | Szente Varga .......... A61F 2/852 |

* cited by examiner

*Primary Examiner* — Ashley L Fishback
*Assistant Examiner* — Chima U Igboko
(74) *Attorney, Agent, or Firm* — Vista IP Law Group, LLP

(57) ABSTRACT

An extravascular access system includes a tubular stent configured to be deployed in a blood vessel, the stent having a sidewall and a proximal end opening and an internal scaffolding comprising one or more structural members, and an elongate access catheter having a distal end portion configured to access the blood vessel wherein when the stent is deployed in the blood vessel, and the distal end portion of the catheter is inserted into the proximal end opening of the stent, the one or more internal structural members of the stent deflect the distal end portion of the catheter towards a wall of the blood vessel.

15 Claims, 14 Drawing Sheets

DIRECTIONAL STENT FOR ACCESSING EXTRAVASCULAR SPACES

RELATED APPLICATION DATA

This application claims the benefit of priority to provisional application Ser. No. 62/854,684, filed on May 30, 2019.

FIELD OF THE INVENTION

The disclosed inventions are generally directed to minimally invasive endovascular surgical procedures and devices.

BACKGROUND

There has been significant progress made in recent decades in the development and practice of minimally invasive surgical devices and procedures. As used herein, "minimally invasive" refers to the use of surgical devices and implants that access the body via the vasculature via arterial or venous access in the groin or neck area, as opposed to more invasive traditional procedures that access the body more directly through percutaneous/solid tissue incisions and cutting and/or boring through bones, as needed to access the internal area of the body on which the procedure is performed. Minimally invasive may also refer to the to the use of surgical devices and implants that access the body via other natural body orifices and tubular structures, such as the esophagus, intestines, bronchial passageways, etc. Percutaneous access through the skin into solid tissue, e.g., for accessing the liver, prostate or lungs, e.g., using a trocar and stylet, may also be considered minimally invasive.

However, some areas of the body, in particular within the brain and immediately surrounding areas within the skull, remain difficult to access via the vasculature due to the extremely small and tortuous blood vessels and bony sinuses. Devices deployed through catheters (which themselves are deployed over guidewires) become difficult to navigate, especially when sharp turns and penetration through bony and dural tissue is required. As such, many neurosurgical procedures may only be performed by cutting through the scalp and skull to reach these areas.

As such, there is an ongoing need for minimally invasive neurosurgical devices that can access hard to reach areas within the brain/skull.

SUMMARY

In accordance with a first aspect of the disclosed inventions, embodiments of a neurovascular venous access system are provided. In an exemplary embodiment, the system includes a tubular stent configured to be deployed in a venous sinus, the stent having a sidewall and a proximal end opening and an internal scaffolding comprising one or more structural members, and an elongate access catheter having a distal end portion configured to access the venous sinus, wherein when the stent is deployed in the venous sinus, and the distal end portion of the catheter is inserted into the proximal end opening of the stent, the one or more internal structural members of the stent deflect the distal end portion of the catheter towards a wall of the venous sinus. In alternative embodiments, directional stent may be configured for, and used in, procedures accessing body lumens other than blood vessels.

In some embodiments, the one or more internal structural members of the stent deflect the distal end portion of the catheter out a distal end opening of the stent. In other embodiments, the one or more internal structural members of the stent deflect the distal end portion of the catheter through an opening in the sidewall of the stent. In such embodiments, the one or more internal structures of the stent may deflect the distal end portion of the catheter through the sidewall opening of the stent at an angle that is approximately 45° or 90° relative to the longitudinal axis of the stent, or at a different desired angle depending on the procedure being performed. Without limitation, the angle may be only slight, e.g., in a range of 5°-20°, and greater, e.g., 20°-45°, or more. Any angle provided by the internal structures of the stent to deflect the distal end portion of the catheter through a sidewall opening of the stent are considered within the scope of the embodiments disclosed herein.

In an exemplary embodiment, the one or more internal structures of the stent include a first directional loop having a diameter sized to accommodate passage of the distal end portion of the catheter, and wherein the passage of the distal end portion of the catheter through the first directional loop deflects a trajectory of the distal end portion catheter at an angle relative to the longitudinal axis of the stent. The one or more internal structures of the stent may further include a second directional loop having a diameter sized to accommodate passage of the distal end portion of the catheter, and wherein the passage of the distal end portion of the catheter through the first directional loop deflects a trajectory of the distal end portion catheter through the second directional loop. Without limitation, the first directional loop is disposed at a first angle relative to the longitudinal axis of the stent, and the second directional loop is disposed at a second angle relative to the longitudinal axis of the stent, different from the first angle. By way of further example, and without limitation, passage of the distal end portion of the catheter through the second directional loop deflects a trajectory of the distal end portion catheter through the sidewall opening of the stent, wherein the first directional loop is disposed at a first angle relative to the longitudinal axis of the stent, wherein the second directional loop is disposed at a second angle relative to the longitudinal axis of the stent, different from the first angle, and wherein the sidewall opening of the stent is disposed at a third angle relative to the longitudinal axis of the stent, different from the first and second angles. The catheter guidance structures may advantageously be constructed of radiopaque materials to allow for fluoroscopic imaging system guidance. Other image guidance systems may also be employed, and the catheter guidance structures may be selected accordingly, e.g., for use with MR or ultrasonic image guidance systems.

In accordance with a further aspect of the disclosed inventions, neurovascular surgical methods are disclosed herein, In an exemplary embodiment, the neurovascular surgical method includes deploying a directional stent in a venous sinus of a patient via the patient's venous system, and navigating a catheter via the patient's venous system through the venous sinus so that a distal end portion of the catheter is inserted through a proximal end opening of the stent, wherein the one or more internal structural members of the stent deflect the distal end portion of the catheter towards a wall of the venous sinus as the distal end portion of the catheter is inserted through the stent. Without limitation, in some embodiments, the one or more internal structural members of the stent deflect the distal end portion of the catheter out a distal end opening of the stent. In other embodiments, the one or more internal structural members of the stent deflect the distal end portion of the catheter through an opening in the sidewall of the stent as the distal end portion of the catheter is inserted through the stent. Notably, the stent may be designed to be retrieved from a first location and redeployed in a different location during a same or subsequent procedure, and thereafter removed from the body, or left in place temporarily or permanently. For example, the stent may be left in a position to help seal the opening(s) made in the venous sinus wall until they are healed by the body.

The method may further include navigating a tissue penetrating element out of a distal end opening of the catheter through the wall of the venous sinus. In such embodiments, the one or more internal structures of the stent deflect the distal end portion of the catheter through the sidewall opening of the stent such that the tissue penetrating element passes through the wall of the venous sinus at an angle (e.g., 45° or 90° or some other desired angle) relative to a longitudinal axis of the stent, depending on the procedure to be performed.

Other and further aspects and features of the disclosed embodiments will become apparent from the ensuing detailed description in view of the accompanying drawings.

BRIEF DESCRIPTION OF THE DRAWINGS

The foregoing and other aspects of embodiments are described in further detail with reference to the accompanying drawings, wherein like reference numerals refer to like elements and the description for like elements shall be applicable for all described embodiments wherever relevant, and in which.

DETAILED DESCRIPTION

Figure 1:
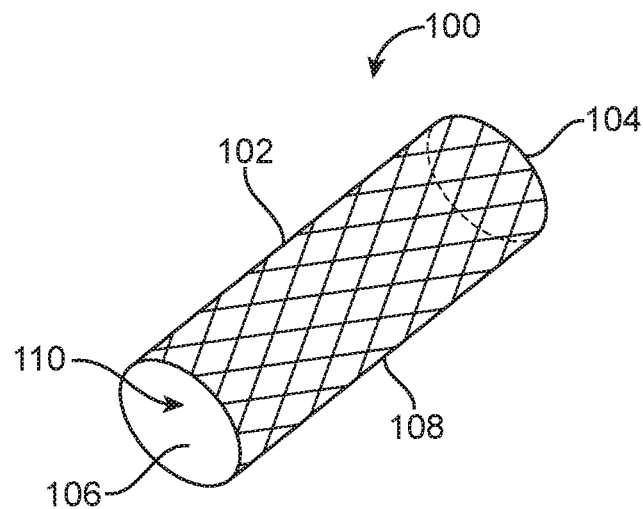
FIG. 1 is a perspective view of an exemplary stent constructed in accordance with one embodiment of the disclosed inventions.

Disclosed and depicted herein are systems and devices for use in performing minimally invasive surgical procedures in extravascular spaces. The disclosed devices can be used in the arterial or venous vasculature to pass through a vessel wall and access a location outside the vasculature. Non-limiting examples include transarterial or transvenous neurosurgery. In the context of minimally invasive neurosurgical procedures, the disclosed systems and devices advantageously avoid the need for drilling a hole in the patient's skull in order to access areas surrounding the brain, as well as brain tissue during a surgical procedure. While the following detailed description relates to transvenous neurosurgical procedures, the disclosure is provided for purposes of explanation and illustration only, and it should be appreciated that the disclosed systems and devices can be used elsewhere in the arterial or venous vasculature to access an extravascular location by passing through a blood vessel wall. For example, alternate embodiments of the directional stent may be configured specifically for performing directional liver biopsies, prostate biopsies, and/or esophagus procedures.

In particular, disclosed herein are embodiments of a directional stent for enabling transvenous access of any region of the brain from a femoral or a brachial or more proximal site in a minimally invasive fashion. The directional stent will enable delivery of a number of neurovascular procedures and therapies, both acute and chronic, using a low-profile system.

Also disclosed herein are embodiments of endovascular methods to pierce a venous sinus wall and direct, in a vectorial fashion, a catheter, needle, and/or other device or implant into the brain tissue to achieve treatment or diagnostic effect. Further disclosed herein are embodiments of a stent assembly that initially stabilizes and scaffolds an entry site into the brain tissue. The disclosed stent assembly provides rotational, angular and translational controls. The length of the catheter, needle, or implant provides depth controls. With these rotational, angular, and depth controls, access to any structure in, or adjacent to, the brain is facilitated. Radiopaque markers may be placed at desirable locations on the stent to facilitate imaging by the operator to ensure the stent is in the desired position and orientation prior to inserting the catheter therethrough. A stent system is deployed (temporarily or permanently) in the cerebral venous sinus system to facilitate and guide the transvenous navigation of a catheter inside the skull (intracranial), as well as below the skull and above the dural (e.g., extradural/epidural) in addition to, without limitation, intradural/subdural and intra-parenchymal (into brain tissue) and intraventricular (into a ventricle) and intracisternal (into a CSF cistern) compartments, including the cerebral and cerebellar tissue and ventricular system. The stent guidance system enables accurate and adjustable navigation of the catheter across the vessel wall in a directed trajectory into various parts of the brain, including the subdural, subarachnoid, intracerebral, and intraventricular compartments.

In one embodiment, the stent is shaped to fit preferentially in a certain location of the transverse sigmoid sinus by virtue of its strut design, such as (without limitation) strut thickness variation, spacing, orientation and pattern. The stent system includes a torquable and rotatable element that enables, once the stent is in a desired position, guidance of the catheter along a chosen trajectory to arrive a desired position. This guidance system enables a transvenous catheter-based treatment process, such as infusion, suction, or deployment of therapeutic agents such as radioactive seeds, stem-cell or sRNA-based therapy. The system can also be used to deploy an intraventricular tube to enable control of obstructive or communicating hydrocephalus, and to instill therapeutic agents in the intraventricular space. One of the advantages of this system and method is that it avoids drilling through the skull to access the brain tissue and surrounding cavities and structures.

A transvenous approach through a venous sinus of the brain can be used to reach virtually any area of the skull by using a specially designed directional stent, which is able to guide a catheter in a rotational and directional fashion following transvenous access. Technologies are presented for controlled access of the wall of the venous sinus, directional and rotational control of access point, and trajectory and depth of penetration using x-ray/MR fusion guidance. A series of minimally invasive alternatives to current treatments using this transvenous transfemoral route are discussed below. Fluoroscopic (x-ray) imaging of the stent may be employed to inform the operator based on radiopaque markers located on the stent body about the rotational and directional vectors, and this can allow the operator to adjust trajectory in an interactive fashion before penetration and during advancement along the vector(s). Ultrasound and/or optical coherence tomography may also be used as guidance tools providing relatively high resolution for the operator to steer the device into position.

FIG. 1 depicts a stent 100 having a hollow cylindrical body 102 with an open distal end 104, an open proximal end 106, a sidewall 108, and a lumen 110 extending therebetween. The stent 100 may be positioned in a venous sinus and used to stabilize and scaffold a device that may be introduced through the stent 100 and that may pierce the venous sinus wall after exiting the distal end 104 of the stent 100. The stent 100 has a collapsed delivery configuration and an expanded deployed configuration. In the embodiments disclosed herein, the stent is self-expanding, but in alternative embodiments the stent could be mechanically expanded, as is well-known in the art.

Figure 2:
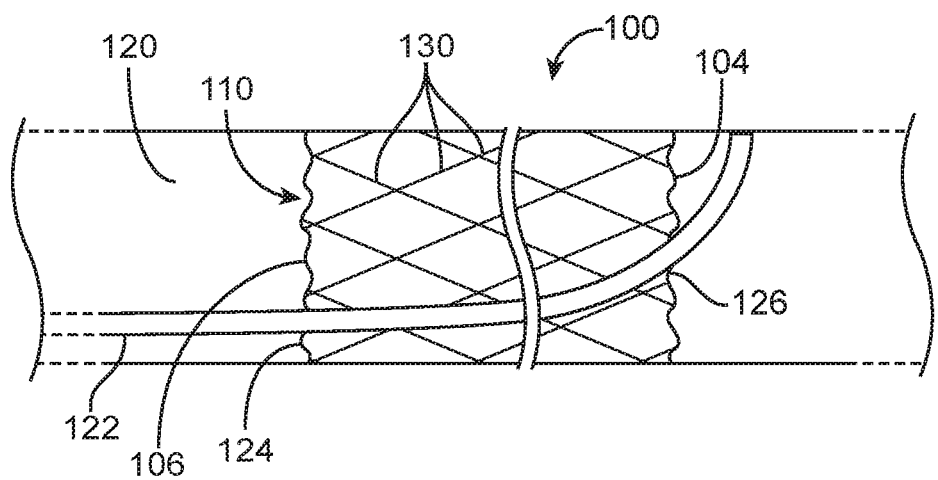
FIG. 2 is a partial cross-sectional side view of the stent of FIG. 1 deployed in a venous sinus, including a catheter deployed through the stent.

With reference to FIG. 2, wherein the stent 100 is shown positioned in a venous sinus 120 and a tool in the form of a catheter 122, is directed through the stent 100 to make contact with the wall of the venous sinus 120. The lumen 110 of the stent 100 includes a plurality of wires, scaffolding, or other such structures 130 that are rigid enough to support and direct the tool 122 to a desired exit point 126. The interior wires or scaffolding 130 are arranged in a manner that provides a pathway for the tool 122, such that the tool 122 enters the stent 100 at the entry point 124 on the proximal end 106 of the stent 100, is steered towards the exit point 126, and exits the stent 100 at the exit point 126 on the distal end 104 of the stent 100.

Figure 3:
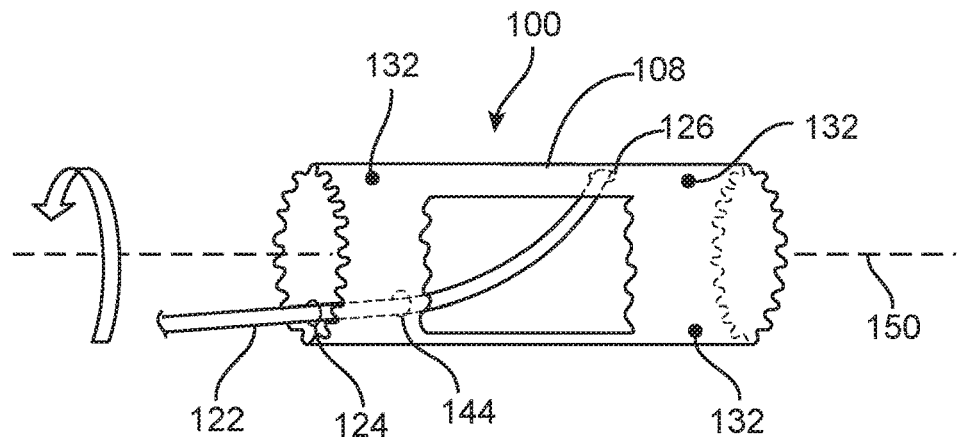
FIG. 3 is a partial cross-sectional side view of the stent of FIG. 2, with the catheter positioned therein.

Referring now to FIG. 3, the stent 100 is depicted with the tool (catheter) 122 disposed therein. As discussed above, the stent 100 includes inner structures 144 that are located and rigid enough to provide a pathway for guiding the tool (catheter) 122 to traverse through the stent 100, from the entry point 124 to the exit point 126. The stent 100 may be provided with one or more radiopaque markers 132 disposed on the sidewall 108 in order to show, using imaging, where in 3D space the stent 100 is positioned within the body (e.g., in a neuro venous sinus), as indicated by the arrow. Thus, the surgeon can verify that the stent 100 is correctly positioned before deploying the tool (catheter) 122 through the stent 100. The stent 100 is preferably rotatable, so that the surgeon may rotate the stent 100 until the exit point 126 is in a desired direction and/or orientation. The stent 100 may also be re-sheathable so that, after the tool (catheter) 122 is deployed through the stent 100, the stent 100 may be re-sheathed and removed from the patient.

Figure 4A:
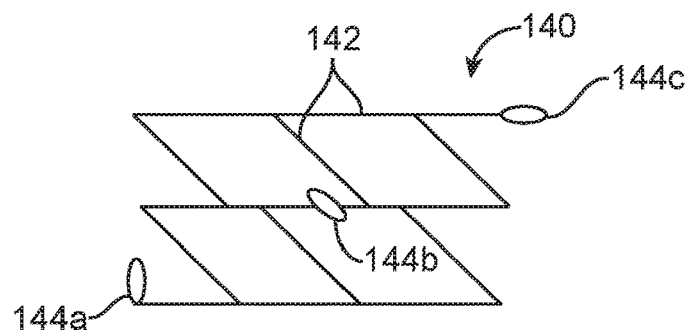
FIG. 4A illustrates an embodiment of the inner structure of the stent of FIG. 1.
Figure 4B:
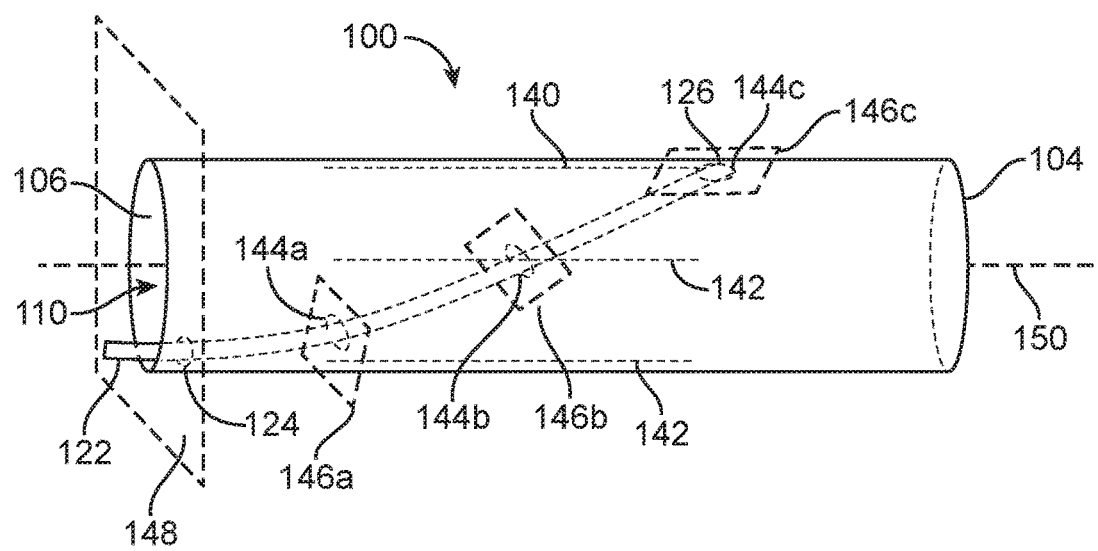
FIG. 4B is a partial cross-sectional view of the stent of FIG. 2, including the catheter deployed there through, and illustrating inner structures of the stent through which the catheter passes, in accordance with embodiments of the disclosed inventions.

In one embodiment, shown in FIGS. 4A and 4B, the stent 100 includes an inner structure 140 made out of wires 142 or other similarly rigid structure(s). The structure 140 further includes loops 144a, 144b, 144c fixedly coupled to the wires 142. As shown in FIG. 4B, the proximal loop 144a is preferably parallel to the proximal opening 106 of the stent 100, i.e., a plane 146a in which the proximal loop 144a lies is substantially parallel to a plane 148 of the proximal opening 106. In this manner, a tool (such as a catheter) 122 inserted into the proximal end 106 of the stent 100 will be aligned with (orthogonal to), and subsequently inserted into, the proximal loop 144a. Structures 140 within the lumen 110 of the stent 100 guide the tool 122 from the proximal loop 144a towards the middle loop 144b, which is positioned at and angle relative to the longitudinal axis 150 of the stent 100. For example, a plane 146b of the middle loop 144b may be at an angle of approximately 45 degrees relative to the plane 146a of the proximal loop 144a. The distal loop 144c is approximately parallel to the longitudinal axis 150 of the stent 100. That is, a plane 146c of the distal loop 144c is parallel to the longitudinal axis 150 of the stent 100 and perpendicular to the plane 148 of the proximal opening 106 in the stent 100. In this manner, the loops 144a, 144b, 144c may act as a ramp and form a pathway to guide the tool 122 from the entry point 124 to the exit point 126 of the stent 100.

Figure 5A:
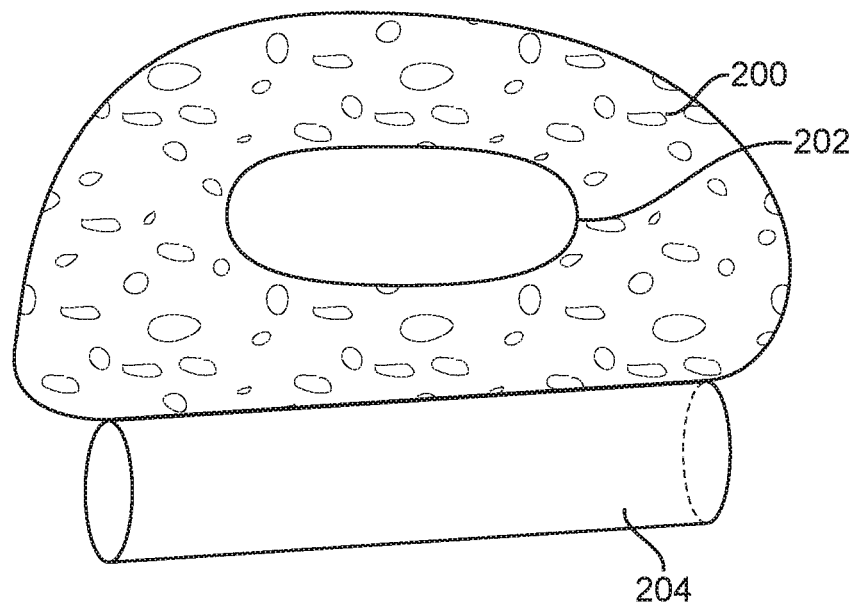
FIGS. 5A-5E illustrate steps in a method for accessing brain tissue using the stent of FIG. 1.

FIGS. 5A-5E depict steps of an exemplary procedure for deploying the stent 100 in a venous sinus 204. FIG. 5A depicts brain tissue 200, including a ventricle 202, and the venous sinus 204.

Figure 5B:
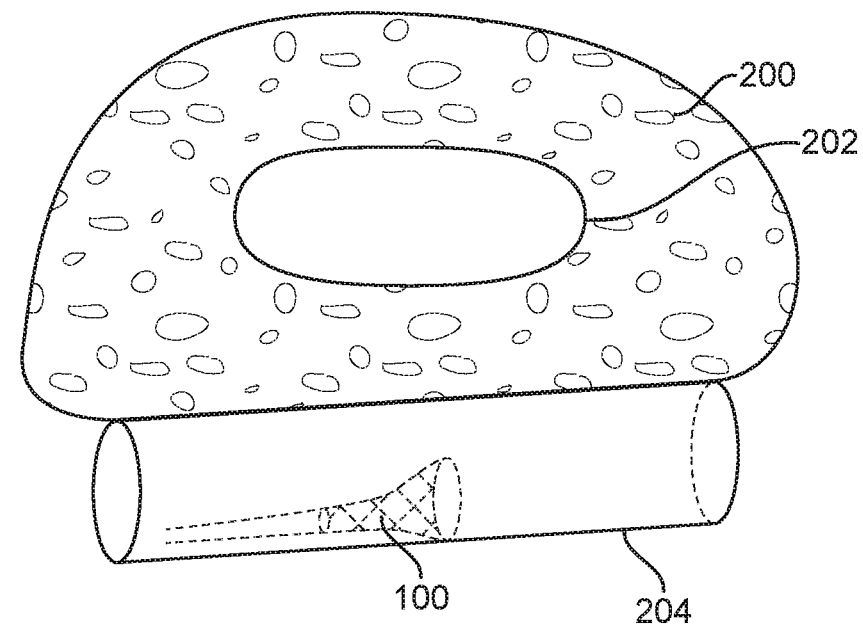

In FIG. 5B, the stent 100 is in the beginning stages of deployment within the venous sinus 204. Known stent deployment tools and procedures may be used to deploy the stent 100.

Figure 5C:
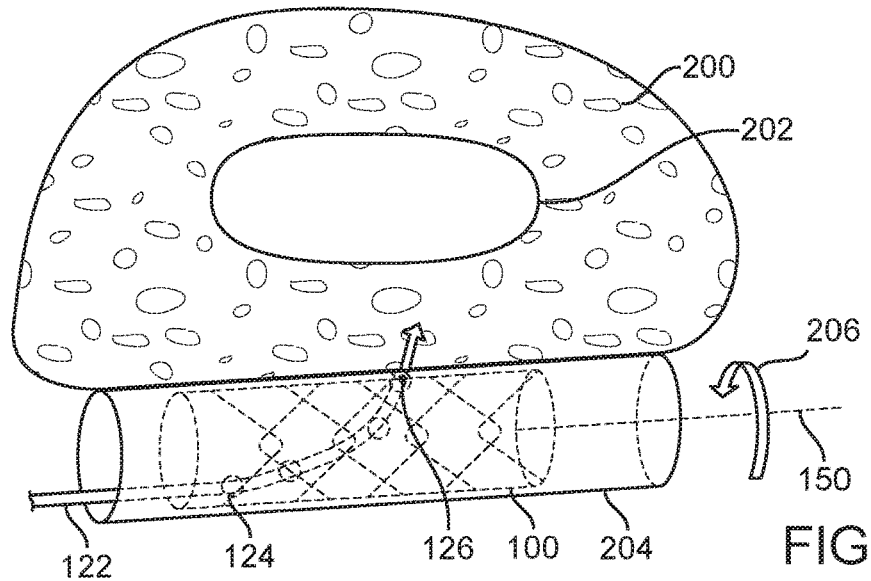

In FIG. 5C, the stent 100 is fully deployed in the venous sinus 204. The stent 100 may be rotated, as indicated by arrow 206, relative to the venous sinus 204 before, during, or after deployment in order to position the stent 100 so that the tool exit point 126 is in a desired location. The tool 122 is then inserted through the stent 100. The distal end of the tool 122, steered by the stent 100 makes contact with the sidewall of the venous sinus 204.

Figure 5D:
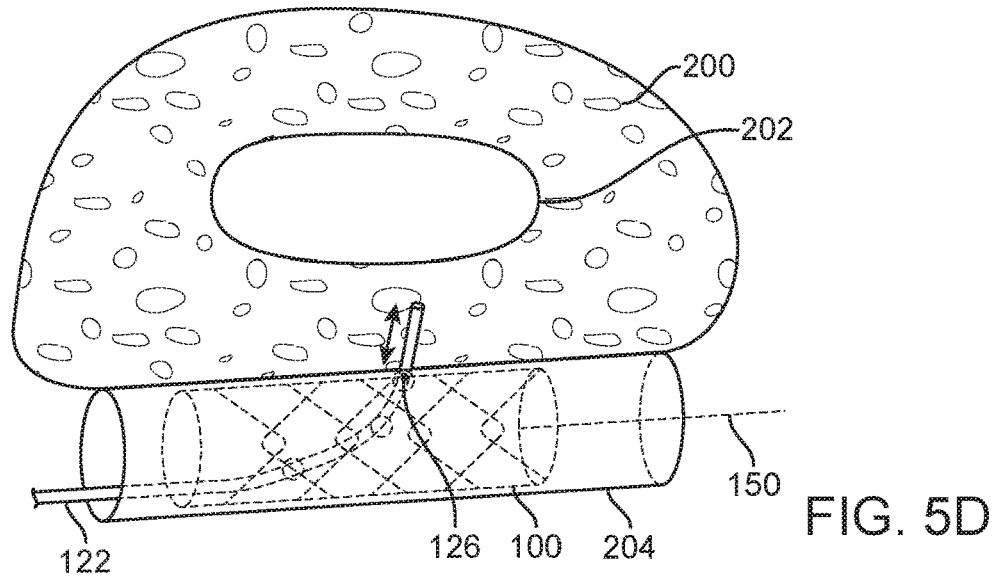
Figure 5E:
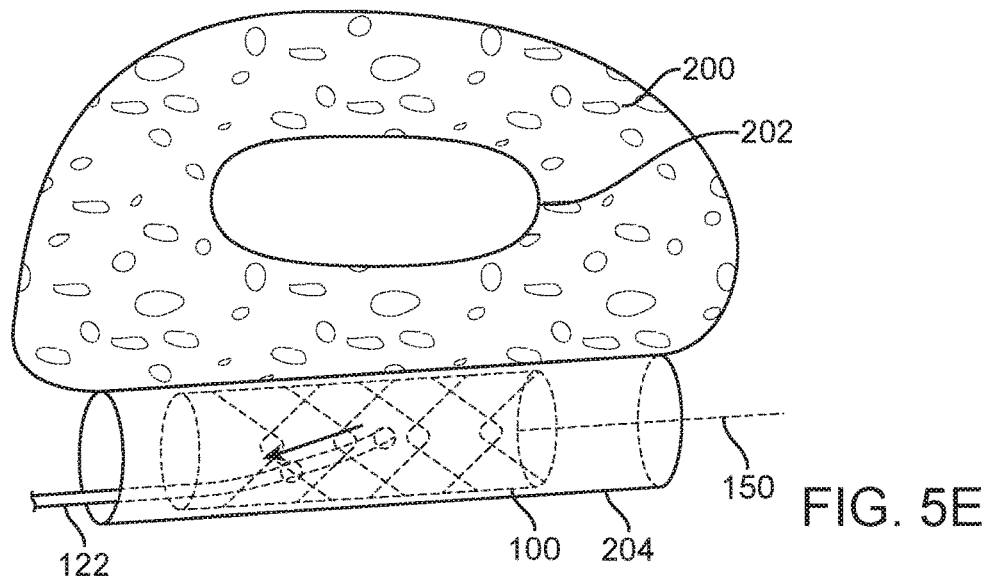

In FIG. 5D, the tool 122 punctures a sidewall of the venous sinus 204 in order to access the brain tissue 200 and/or ventricle 202. After completion of the procedure, the tool 122 is withdrawn from the brain tissue 200 and back into the stent 100, as shown in FIG. 5E. The stent 100 may be removed upon completion of the procedure, using well known stent removal procedures. Alternatively, the stent 100 may remain implanted in the venous sinus 204 for use in future procedures, and/or the stent 100 may be made is bioresorbable material and dissolve after a sufficient period of time.

Figure 6:
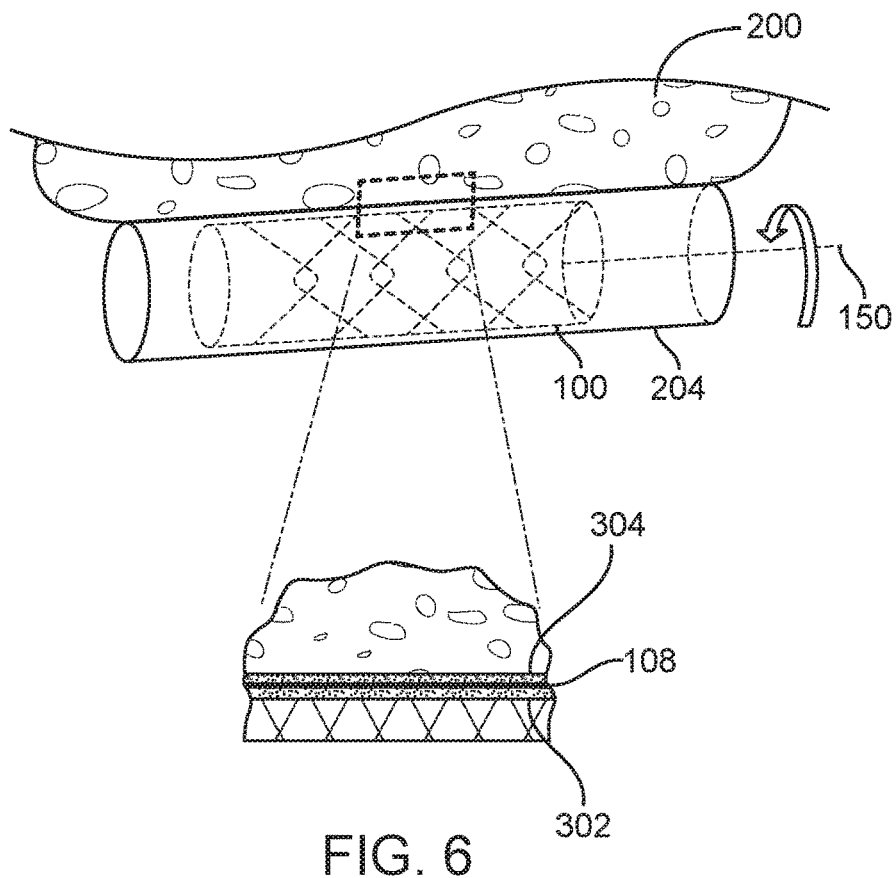
FIG. 6 is a cross-sectional view of a sidewall of a stent deployed in a sinus cavity, in accordance with one embodiment of the disclosed inventions.

As shown in FIG. 6, the stent 100 may include an inner coating 302 and/or an outer coating 304 on the sidewall 108 of the stent 100. For example, the outer coating 304 may be thrombogenic in order to seal the dura when the tool 122 punctures the wall of the venous sinus 204 and the dura. The inner coating 302 may have anti-coagulant, anti-thrombosis properties to prevent blood from coagulating inside the stent 100. The stent 100 may be dissolvable.

Figure 7:
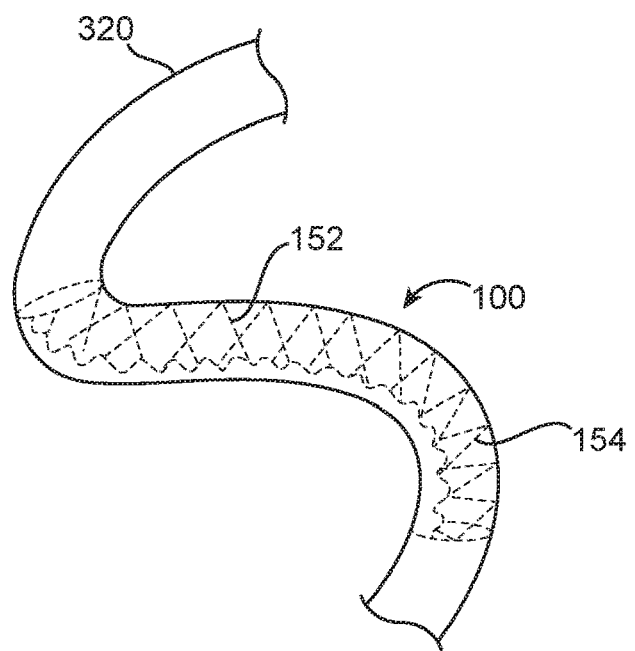
FIG. 7 illustrates a stent deployed in a tortuous sigmoid sinus region, in accordance with one embodiment of the disclosed inventions, in which the stent comprises segments having varying stiffnesses.

In another embodiment, shown in FIG. 7, the stent 100 has segments of varying stiffness. For example, the stent 100 has portions 152 that are stiffer and portions 154 that are more flexible. The varying stiffness may be achieved by using different strut thickness distribution and shaping. Notably, the variation may not just be along the length of the stent, but also along its angle, i.e., 0-45 degrees may be stiffer or varying differently from the remaining 45-360 degrees, when looking down the barrel of the stent. Such a stent having varying stiffness along the length thereof may be useful, for example, in the tortuous anatomy of the transverse sigmoid sinus region 320. This embodiment is advantageous in that it achieves better navigation and has greater stability when deployed. The varying stiffness regions may also facilitate re-sheathing of the stent. The varying stiffness regions may be custom designed for a pre-determined location in the venous system.

The stent 100 may be customized, depending on the desired pathway of the tool 122. A customized stent can provide a desired entry point and exit point for the tool (e.g., catheter) 122. Additionally, or alternatively, the stent 100 may be provided in a kit that includes several stents, each one providing a different pathway for the tool that is inserted therethrough. The medical provider is then able to choose which stent from the kit to use, depending on the procedure being performed and the desired entry point and exit point for the tool that is deployed through the stent.

Examples of various procedures using the stent 100 will now be discussed with reference to FIGS. 8-16.

Figure 8:
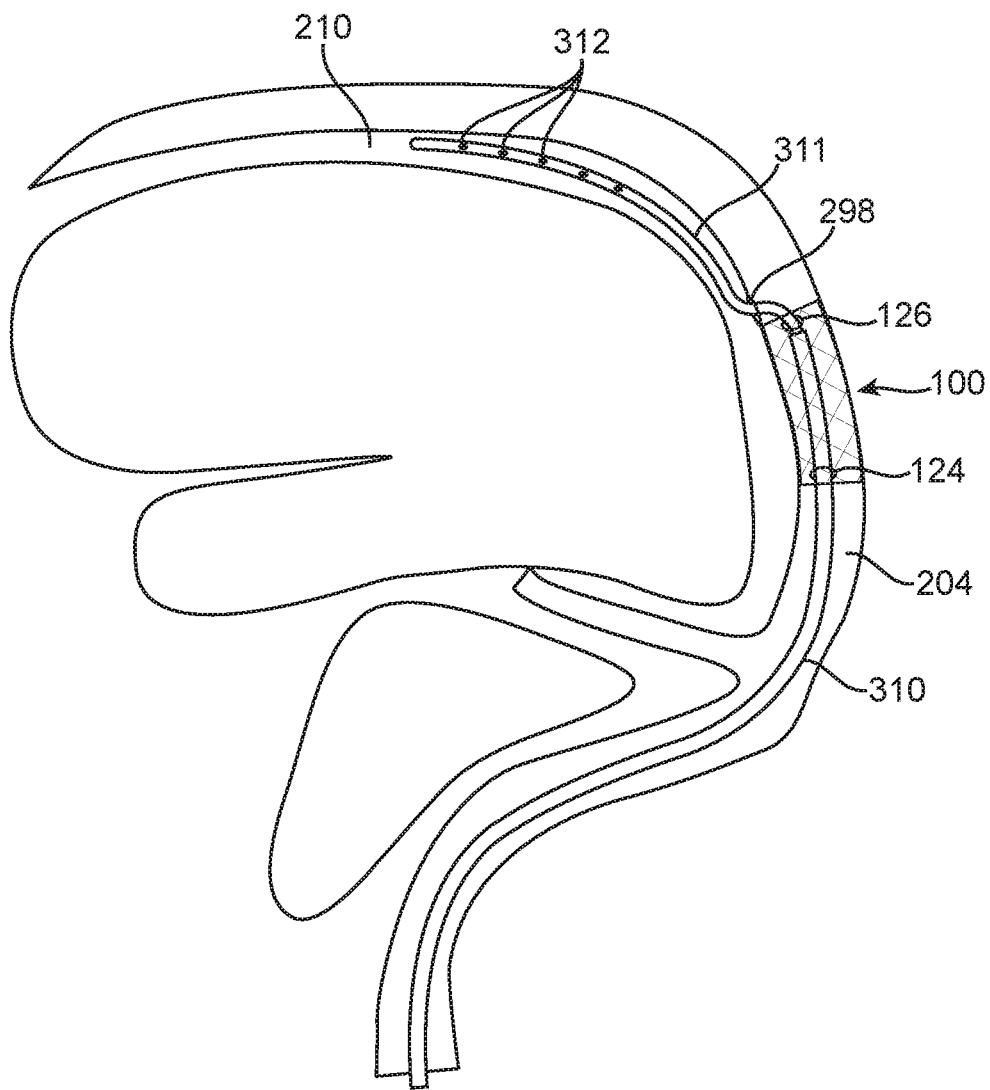
FIGS. 8-16 illustrate various procedures performed on brain tissue that can be accessed using embodiments of the stent.

In one embodiment, shown in FIG. 8, the stent 100 is positioned in the venous sinus 204 using known stent deployment tools and procedures. After the stent 100 is properly positioned, a delivery catheter 310 is guided into the stent 100 through a proximal stent entry point 124, within the interior of the stent, an electrode lead 311 is advanced out of an open end of the delivery catheter 310, and out a distal stent exit point 126, which redirects the electrode lead 311 through an opening 298 in an adjacent wall of the venous sinus 204 in order to access the subdural space 210. The lead 311 carrying electrodes and grids 312 is deployed through the catheter 310 and positioned in the subdural space 210. As such, using the stent 100 for transvenous access to the subdural space 210, subdural electrodes and grids 312 may be deployed through a catheter 310 that is guided through the stent 100. Such electrodes and grids 312 may be used for seizure surgery monitoring, deployment of a neural interface for prostheses, or the like.

Figure 9:
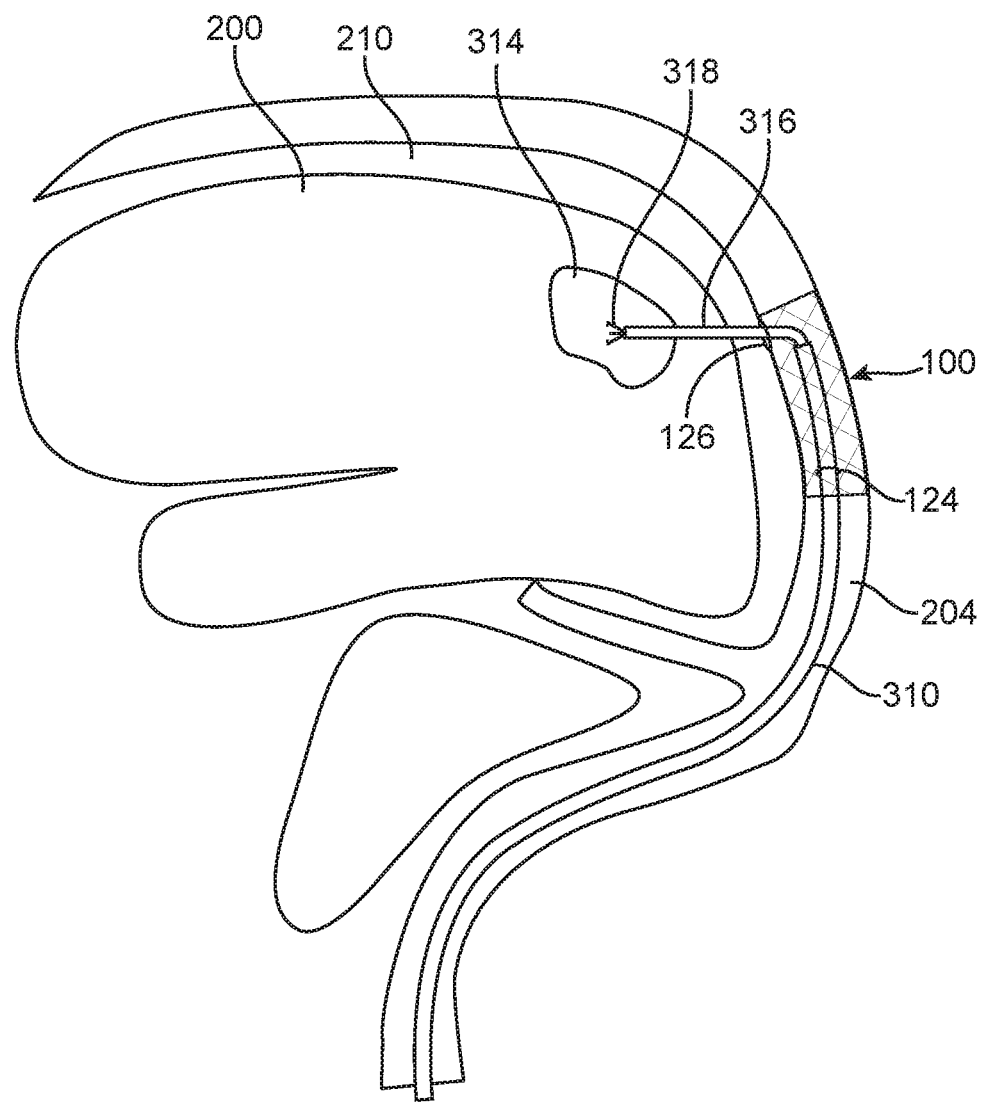

As shown in FIG. 9, the stent 100 may be used in a brain tumor biopsy procedure. Using transvenous access and directional stent technology, MR-Xray fusion technology enables the targeting of a tumorous region in the brain for biopsy. Using known stent deployment tools and procedures, the stent 100 is positioned in the venous sinus 204 near the site of a tumor 314. Next, a catheter 316, such as a transcortical working port, is deployed through a delivery catheter 310 positioned in the stent 100. The unique design of the stent 100 provides a pathway that steers the catheter 316 and/or the delivery catheter 310 from the stent entry point 124 to the stent exit point 126 adjacent to the wall of the venous sinus 204. The catheter 316 then punctures the wall of the venous sinus 204 and is directed through brain tissue 200 to the tumor 314. Forceps 318 deployed through the catheter 316 are used to obtain a sample of tissue from the tumor 314.

Figure 10:
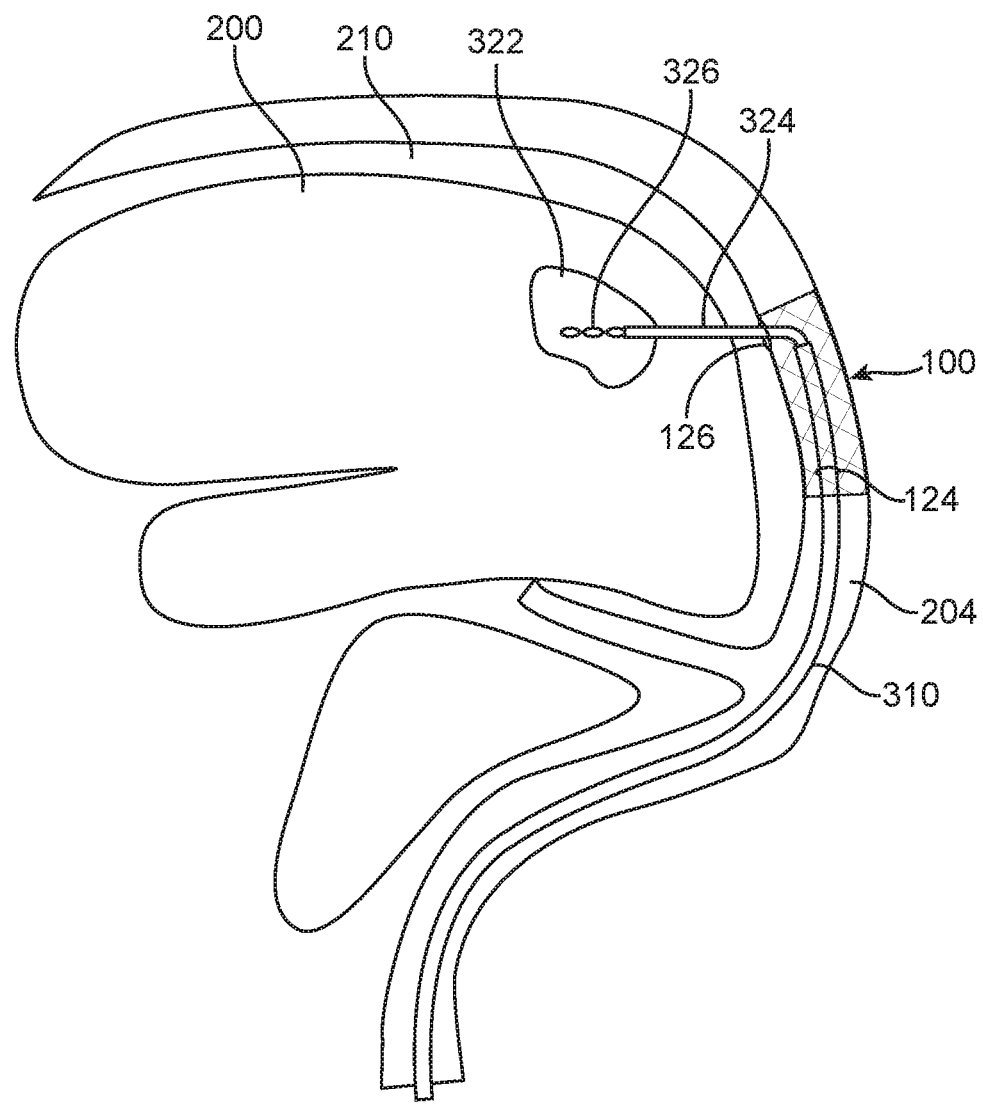

In another embodiment, shown in FIG. 10, the stent 100 may be used for an intra-tumor radioactive seed treatment. Using transvenous access and directional stent technology, MR-Xray fusion technology enables the implantation of radioactive beads for treatment of a tumorous region in the brain. Specifically, in such a procedure, the stent 100 is deployed in the venous sinus 204 near the site of a brain tumor 322. A catheter 324, such as a transcortical working port, is directed through a delivery catheter 310 positioned in the stent 100. The unique design of the stent 100 provides a pathway that steers the catheter 324 and/or the delivery catheter 310 from the stent entry point 124 to the stent exit point 126 adjacent to the wall of the venous sinus 204. The catheter 324 then punctures the wall of the venous sinus 204 and is pushed straight until the distal end of the catheter 324 is positioned in the tumor 322. Radioactive seeds 326 are then deployed out of the distal end of the catheter 324 and into the tumor 322.

Figure 11:
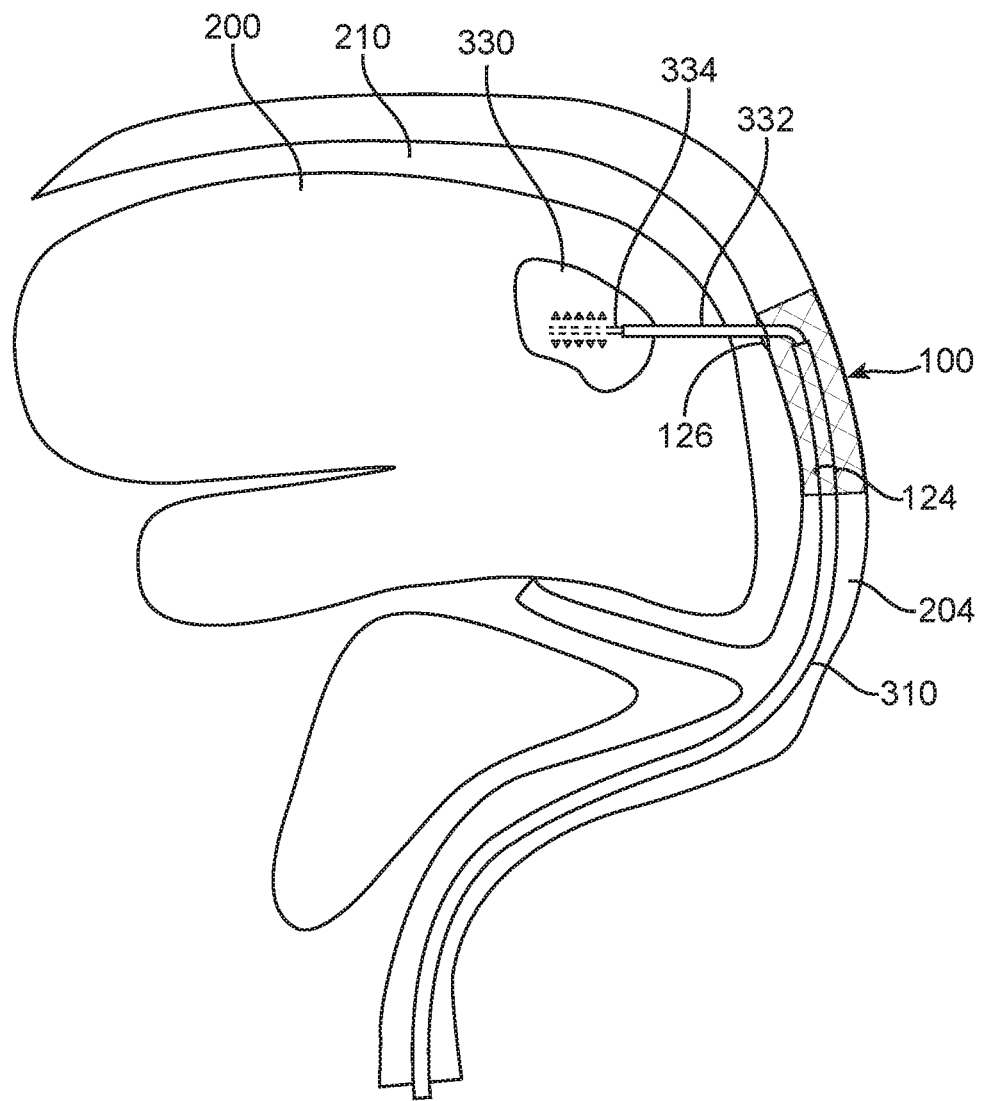

FIG. 11 depicts the stent 100 being used in a procedure to deliver pharmaceutical or biologically active agents to a tumor. Using transvenous access and directional stent technology, MR-Xray fusion technology enables the infusion of pharmaceutical or biologically active agents. Specifically, in such a procedure, the stent 100 is deployed in the venous sinus 204 near the site of a brain tumor 330. A catheter 332, such as a transcortical working port, is directed through a delivery catheter 310 positioned in the stent 100. The unique design of the stent 100 provides a pathway that steers the catheter 332 and/or the delivery catheter 310 from the stent entry point 124 to the stent exit point 126 adjacent to the wall of the venous sinus 204. The catheter 332 then punctures the wall of the venous sinus 204 and is pushed straight until the distal end of the catheter 332 is positioned in the tumor 330. Pharmaceutical or biological therapeutic agent 334 is then infused into the tumor 330 from the distal end of the catheter 332.

Figure 12:
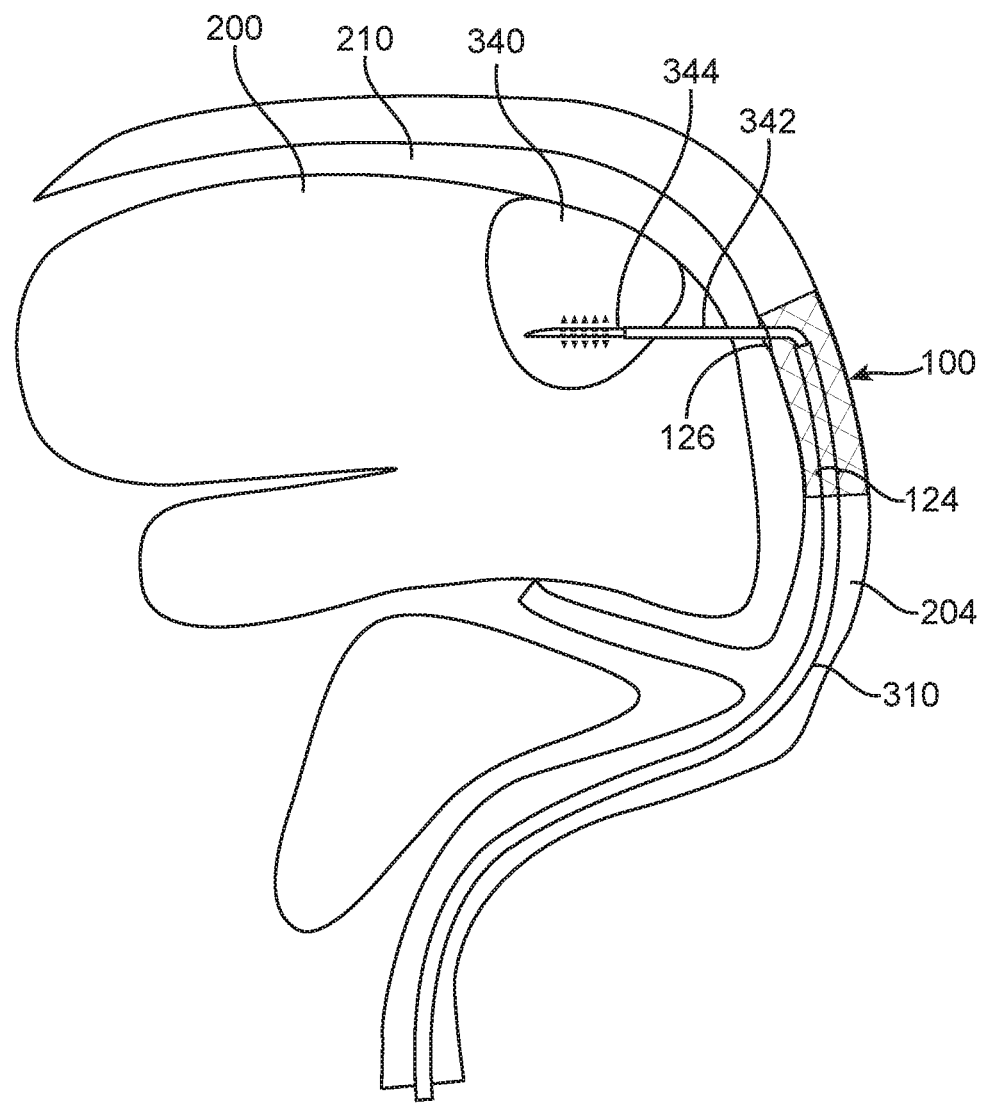

In still another embodiment, shown in FIG. 12, the stent 100 is used in neural stem cell treatment. Using transvenous access and directional stent technology, MR-Xray fusion technology enables the infusion of neural stem cells for treatment of regions affected by stroke or other conditions. Specifically, in such a procedure, the stent 100 is deployed in the venous sinus 204 near an area of stroke 340. A catheter 342, such as a transcortical working port, is directed through a delivery catheter 310 positioned in the stent 100. The unique design of the stent 100 provides a pathway that steers the catheter 342 and/or the delivery catheter 310 from the stent entry point 124 to the stent exit point 126 adjacent to the wall of the venous sinus 204. The catheter 342 then punctures the wall of the venous sinus 204 and is pushed straight until the distal end of the catheter 342 is positioned in the area of stroke 340. Neural stem cells 344 are then injected into the area of stroke 340 through the distal end of the catheter 342.

Figure 13:
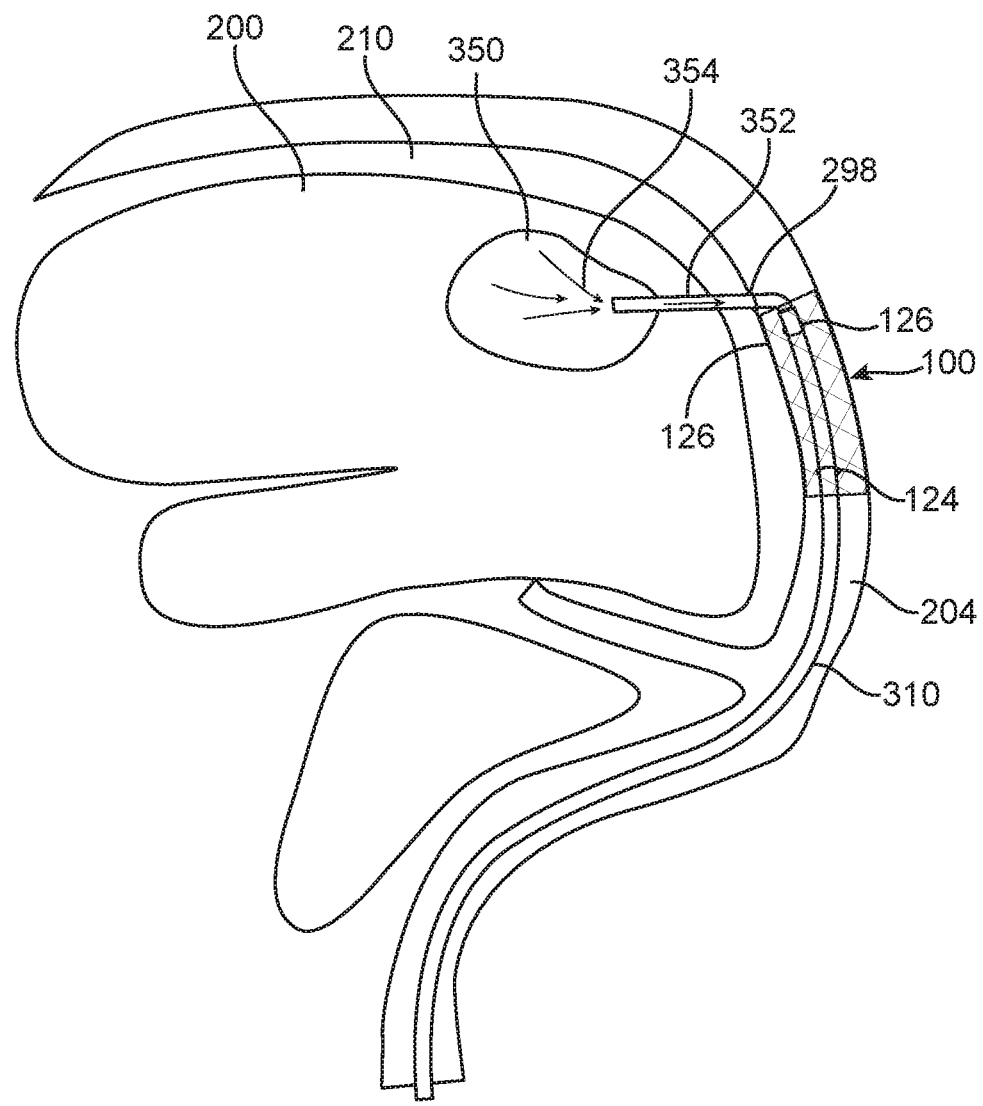

FIG. 13 depicts the stent 100 being used in an intracranial hemorrhage suction procedure. Using transvenous access and directional stent technology, intracranial hemorrhage can be accessed for suction decompression or for instillation of clot dissolver prior to suction. Specifically, in such a procedure, the stent 100 is deployed in the venous sinus 204 near the intraparenchymal hemorrhage area 350. A catheter 352, such as a transcortical working port, is directed through the delivery catheter 310 positioned in the stent 100. The unique design of the stent 100 provides a pathway that steers the catheter 352 and/or the delivery catheter 310 from the stent entry point 124 to the stent exit point 126 adjacent to the wall of the venous sinus 204. The catheter 352 then punctures the wall of the venous sinus 204 at location 298 and is pushed straight until the distal end of the catheter 352 is positioned in the area of the hemorrhage 350. Suction can be applied through the distal end of the catheter 352, as indicated by arrows 354. Additionally, or alternatively, the hemorrhage 350 may be treated, such as with clot dissolver deployed out of the distal end of the catheter 352, prior to, or instead of, applying suction.

Figure 14:
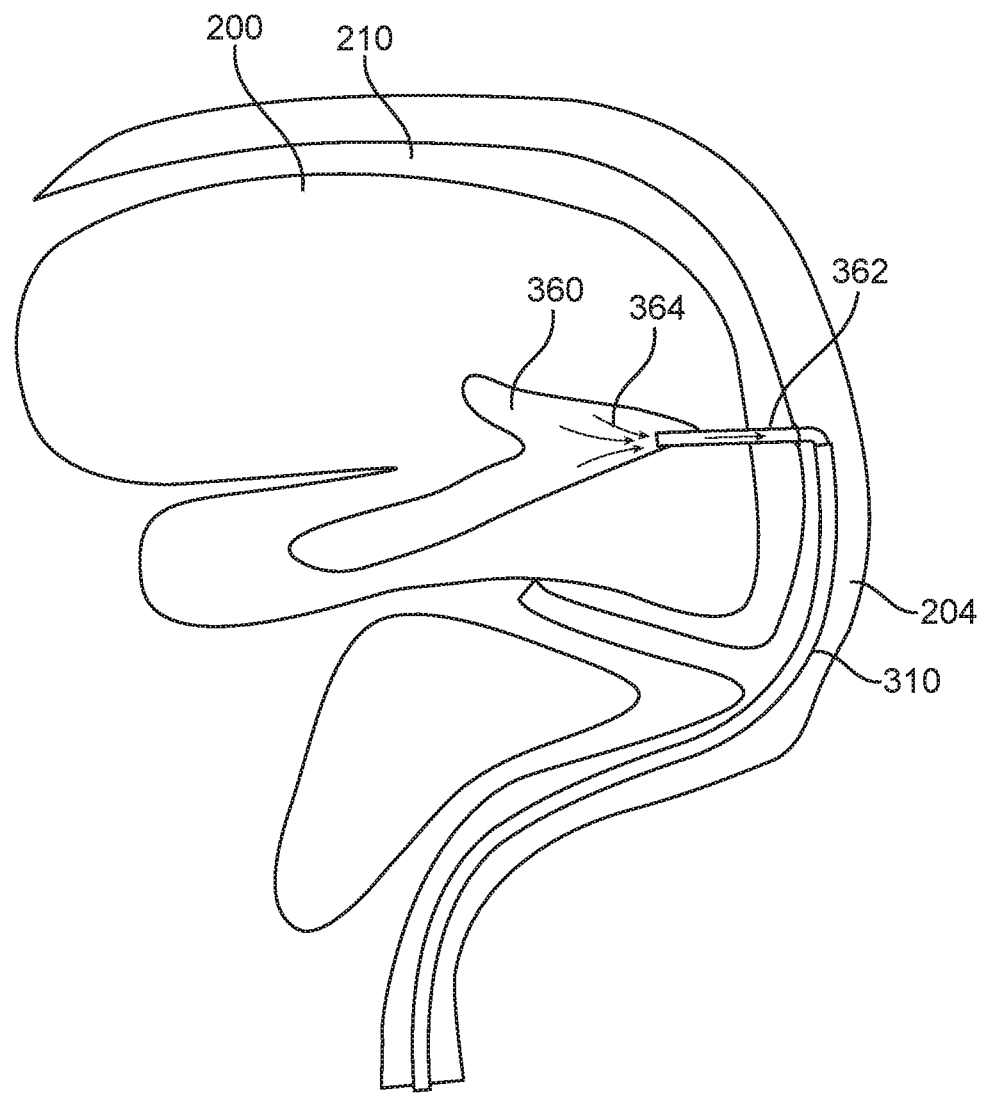

Similar to the embodiment shown in FIG. 13, FIG. 14 depicts the stent 100 being used in an intraventricular hemorrhage suction procedure. Using transvenous access and directional stent technology, intraventricular hemorrhage can be accessed for suction decompression or for instillation of clot dissolver prior to suction. Specifically, in such a procedure, the stent 100 (not shown in FIG. 14) is deployed in the venous sinus 204 near the intraventricular hemorrhage area 360. A catheter 362, such as a transcortical working port, is directed through a delivery catheter 310 positioned in the stent 100. The unique design of the stent 100 provides a pathway that steers the catheter 362 and/or the delivery catheter 310 from the stent entry point to the stent exit point adjacent to the wall of the venous sinus 204. The catheter 362 then punctures the wall of the venous sinus 204 and is pushed straight until the distal end of the catheter 362 is positioned in the area of the intraventricular hemorrhage 360. The stent 100 may be re-sheathed and removed after the catheter 362 is deployed in the desired position. As such, FIG. 14 depicts the intraventricular hemorrhage suction procedure after the stent 100 has been removed. Suction can then be applied through the distal end of the catheter 362, as indicated by arrows 364. Additionally, or alternatively, the hemorrhage 360 may be treated, such as with clot dissolver deployed out of the distal end of the catheter 362, prior to, or instead of, applying suction.

Figure 15:
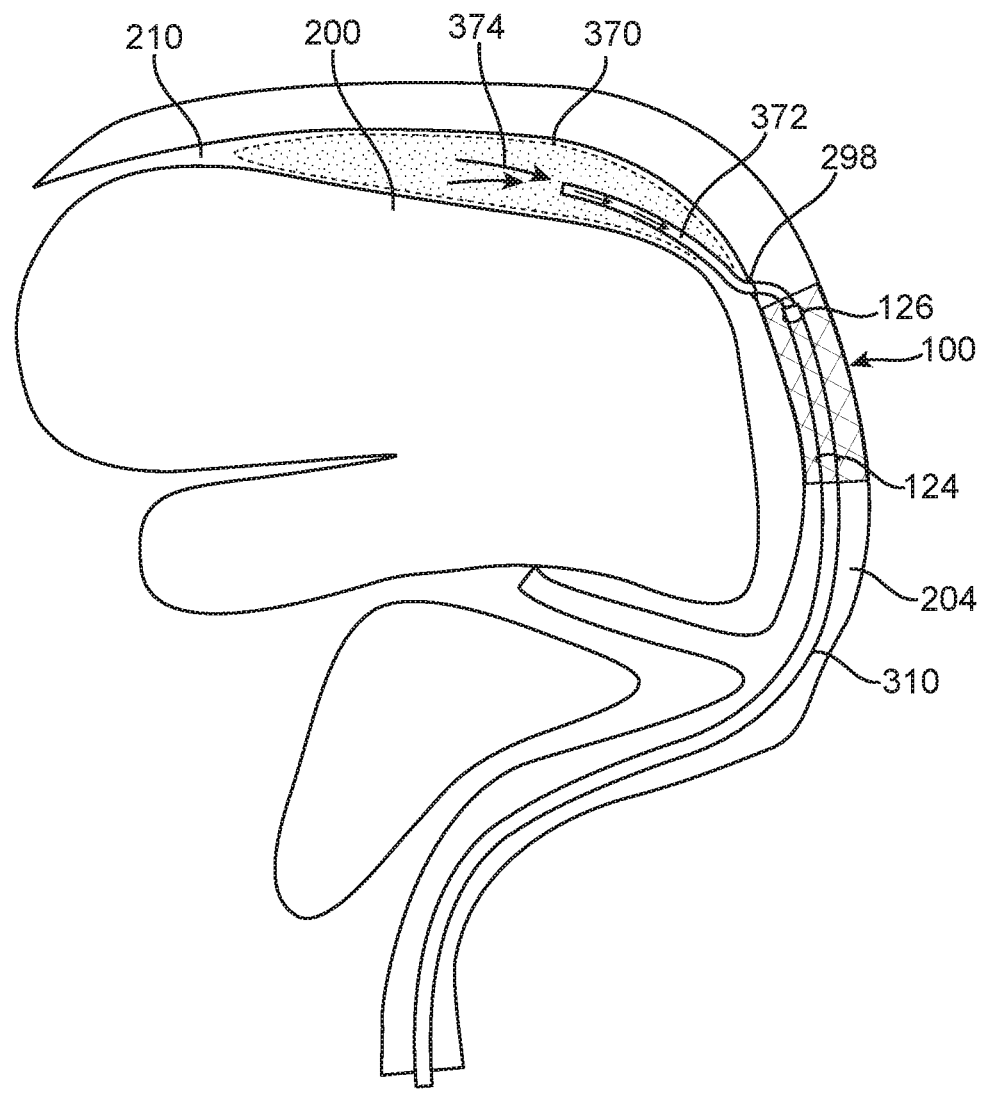

FIG. 15 depicts the stent 100 being used in a subdural hemorrhage suction procedure. Using transvenous access and directional stent technology, subdural hemorrhage can be accessed for suction decompression or for instillation of clot dissolver prior to suction. Specifically, in such a procedure, the stent 100 is deployed in the venous sinus 204 near the subdural hemorrhage area 370. A catheter 372, such as a transcortical working port, is directed through a delivery catheter 310 positioned in the stent 100. The unique design of the stent 100 provides a pathway that steers the catheter 372 and/or the delivery catheter 310 from the stent entry point 124 to the stent exit point 126 adjacent to the wall of the venous sinus 204. The catheter 372 then punctures the wall of the venous sinus 204 at location 298 and is guided through the subdural space 210 until the distal end of the catheter 372 is positioned in the area of the hemorrhage 370. Suction can be applied through the distal end of the catheter 372, as indicated by arrows 374. Additionally, or alternatively, the hemorrhage 370 may be treated, such as with clot dissolver deployed out of the distal end of the catheter 372, prior to, or instead of, applying suction.

Figure 16:
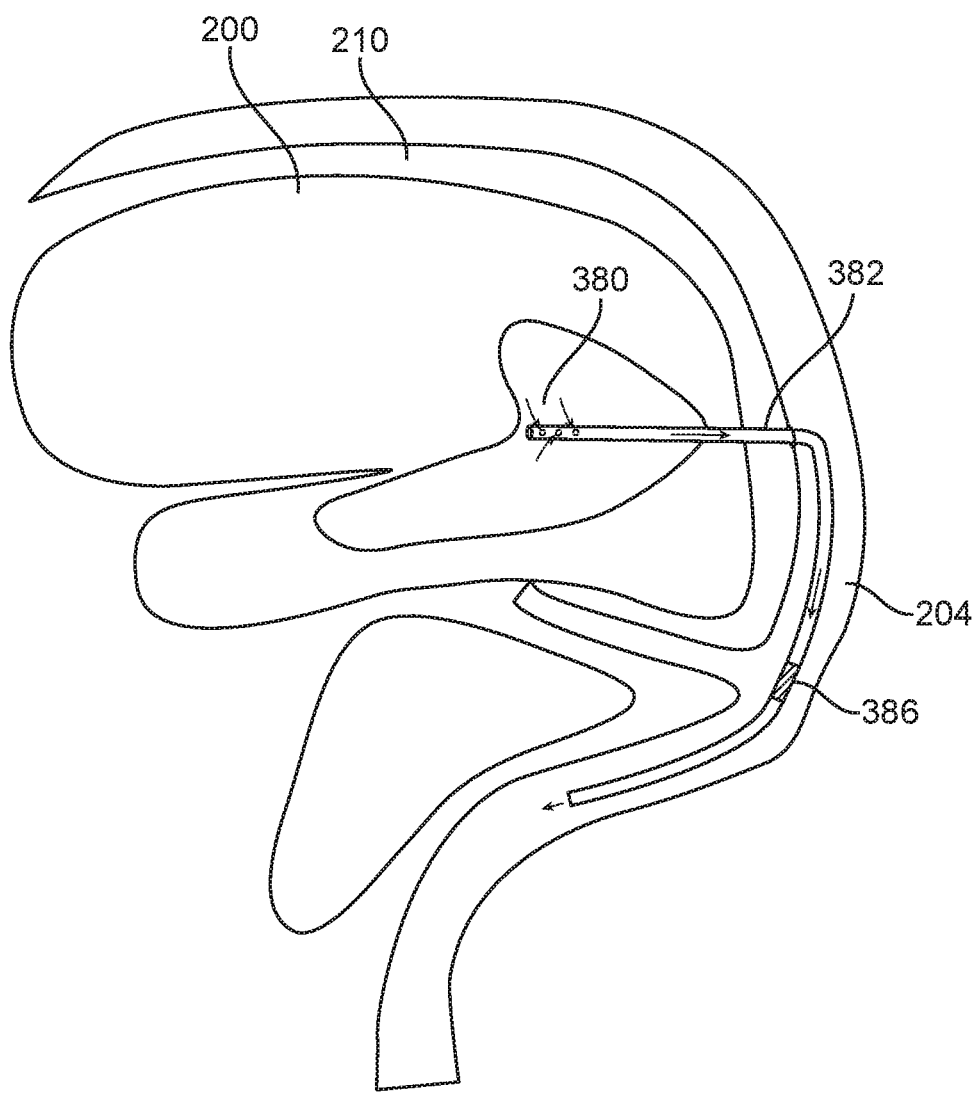

FIG. 16 depicts the stent 100 being used in a procedure for transvenous deployment of a ventriculo-sinus shunt for hydrocephalus. Using transvenous access and directional stent technology, a ventricular catheter can be advanced into the lateral or frontal ventricle and then be deployed into the transverse/sigmoid sinus. A similar approach can be used to deliver pharmacological agents to subdural, subarachnoid, intraventricular, or intraparenchymal locations from a transvenous approach. Specifically, in such a procedure, the stent 100 (not shown in FIG. 16) is deployed in the venous sinus 204 near an area 380 having cerebrospinal fluid. A catheter 382, such as a transcortical working port, is directed through the stent 100. The unique design of the stent 100 provides a pathway that steers the catheter 382 from the stent entry point to the stent exit point adjacent to the wall of the venous sinus 204. The catheter 382 then punctures the wall of the venous sinus 204 and is pushed straight until the distal end of the catheter 382 is positioned in the area 380 of cerebrospinal fluid. The catheter 382 may remain in place while the stent 100 is re-sheathed and removed. The catheter 382 acts as a shunt for draining the cerebrospinal fluid. As such, the catheter 382 may include a valve 386, or slits (not shown) in the sidewall of the catheter 382, to allow cerebrospinal fluid to drain out of the brain, while also preventing blood from flowing into the brain.

While particular embodiments illustrating variations of the many aspects of the disclosed inventions have been disclosed and described herein, such disclosure is provided for purposes of explanation and illustration only. Thus, various changes and modifications may be made to the disclosed embodiments without departing from the scope of the claims. For example, not all of the components described in the embodiments may be necessary for any particular embodiment, and the disclosed inventions may include any suitable combination of the described components. Accordingly, the disclosed inventions should not be limited, except as set forth in the following claims, and their equivalents.

What is claimed is:

1. A neurovascular venous access system, comprising:
   a tubular stent configured to be deployed in a venous sinus, the tubular stent having a sidewall defining a lumen, a proximal end opening, and an internal scaffolding disposed in the lumen and comprising one or more internal structural members; and
   an elongate access catheter having a distal end portion configured to access the venous sinus,
   wherein when the stent is deployed in the venous sinus, and the distal end portion of the catheter is inserted into the proximal end opening of the tubular stent, the one or more internal structural members of the tubular stent deflect the distal end portion of the catheter towards a wall of the venous sinus,
   wherein the tubular stent defines a longitudinal axis, and wherein the one or more internal structural members of the tubular stent deflect the distal end portion of the catheter through an opening in the sidewall of the tubular stent,
   wherein the one or more internal structural members of the tubular stent include a first directional loop having a diameter sized to accommodate passage of the distal end portion of the catheter, and wherein the passage of the distal end portion of the catheter through the first directional loop deflects a trajectory of the distal end portion of the catheter at an angle relative to the longitudinal axis of the tubular stent, and
   wherein the one or more internal structural members of the tubular stent further includes a second directional loop having a diameter sized to accommodate passage of the distal end portion of the catheter, and wherein the passage of the distal end portion of the catheter through the first directional loop deflects a trajectory of the distal end portion catheter through the second directional loop.

2. The neurovascular venous access system of claim 1, wherein the first directional loop is disposed at a first angle relative to the longitudinal axis of the tubular stent, and wherein the second directional loop is disposed at a second angle relative to the longitudinal axis of the tubular stent, different from the first angle.

3. The neurovascular venous access system of claim 1, wherein the passage of the distal end portion of the catheter through the second directional loop deflects a trajectory of the distal end portion catheter through the sidewall opening of the tubular stent.

4. The neurovascular venous access system of claim 3, wherein the first directional loop is disposed at a first angle relative to the longitudinal axis of the tubular stent, wherein the second directional loop is disposed at a second angle relative to the longitudinal axis of the tubular stent, different from the first angle, and wherein the sidewall opening of the tubular stent is disposed at a third angle relative to the longitudinal axis of the tubular stent, different from the first and second angles.

5. An etravascular access system, comprising:
a tubular stent configured to be deployed in a body lumen, the tubular stent having
a sidewall defining a lumen, a proximal end opening, and an internal scaffolding disposed in the lumen and comprising one or more internal structural members; and
an elongate access catheter having a distal end portion configured to access the body lumen,
wherein when the tubular stent is deployed in the body lumen, and the distal end portion of the catheter is inserted into the proximal end opening of the tubular stent, the one or more internal structural members of the stent deflect the distal end portion of the catheter towards a wall of the body lumen,
wherein the tubular stent defines a longitudinal axis, and wherein the one or more internal structural members of the tubular stent deflect the distal end portion of the catheter through an opening in the sidewall of the tubular stent, and
wherein the one or more internal structural members of the tubular stent deflect the distal end portion of the catheter through the sidewall opening of the tubular stent at an angle that is at least 45° relative to the longitudinal axis of the tubular stent.

6. A neurovascular venous access system, comprising:
a tubular stent configured to be deployed in a venous sinus, the tubular stent having a sidewall defining a lumen, a proximal end opening, and an internal scaffolding disposed in the lumen and comprising one or more internal structural members; and
an elongate access catheter having a distal end portion configured to access the venous sinus,
wherein when the stent is deployed in the venous sinus, and the distal end portion of the catheter is inserted into the proximal end opening of the tubular stent, the one or more internal structural members of the tubular stent deflect the distal end portion of the catheter towards a wall of the venous sinus,
wherein the tubular stent defines a longitudinal axis, and wherein the one or more internal structural members of the tubular stent deflect the distal end portion of the catheter through an opening in the sidewall of the tubular stent, and
wherein the one or more internal structural members of the tubular stent deflect the distal end portion of the catheter through the sidewall opening of the tubular stent at an angle that is 5° to 20° relative to the longitudinal axis of the tubular stent.

7. A neurovascular venous access system, comprising:
a tubular stent configured to be deployed in a venous sinus, the tubular stent having a sidewall defining a lumen, a proximal end opening, and an internal scaffolding disposed in the lumen and comprising one or more internal structural members; and
an elongate access catheter having a distal end portion configured to access the venous sinus,
wherein when the stent is deployed in the venous sinus, and the distal end portion of the catheter is inserted into the proximal end opening of the tubular stent, the one or more internal structural members of the tubular stent deflect the distal end portion of the catheter towards a wall of the venous sinus,
wherein the tubular stent defines a longitudinal axis, and wherein the one or more internal structural members of the tubular stent deflect the distal end portion of the catheter through an opening in the sidewall of the tubular stent, and
wherein the one or more internal structural members of the tubular stent deflect the distal end portion of the catheter through the sidewall opening of the tubular stent at an angle that is 20° to 45° relative to the longitudinal axis of the tubular stent.

8. A neurovascular venous access system, comprising:
a tubular stent configured to be deployed in a venous sinus, the tubular stent having a sidewall defining a lumen, a proximal end opening, and an internal scaffolding disposed in the lumen and comprising one or more internal structural members; and
an elongate access catheter having a distal end portion configured to access the venous sinus,
wherein when the stent is deployed in the venous sinus, and the distal end portion of the catheter is inserted into the proximal end opening of the tubular stent, the one or more internal structural members of the tubular stent deflect the distal end portion of the catheter towards a wall of the venous sinus,
wherein the tubular stent defines a longitudinal axis, and wherein the one or more internal structural members of the tubular stent deflect the distal end portion of the catheter through an opening in the sidewall of the tubular stent, and
wherein the one or more internal structural members of the tubular stent deflect the distal end portion of the catheter through the sidewall opening of the tubular stent at an angle that is 45° to 90° relative to the longitudinal axis of the tubular stent.

9. A neurovascular venous access system, comprising:
a tubular stent configured to be deployed in a venous sinus, the tubular stent having a sidewall defining a lumen, a proximal end opening, and an internal scaffolding disposed in the lumen and comprising one or more internal structural members; and
an elongate access catheter having a distal end portion configured to access the venous sinus,
wherein when the stent is deployed in the venous sinus, and the distal end portion of the catheter is inserted into the proximal end opening of the tubular stent, the one or more internal structural members of the tubular stent deflect the distal end portion of the catheter towards a wall of the venous sinus,
the one or more internal structural members comprising a plurality of wires and a plurality of directional loops, wherein each directional loop of the plurality of directional loops is fixedly coupled to at least one wire and respectively angularly oriented to deflect the distal end portion of the catheter towards the wall of the venous sinus.

10. The neurovascular venous access system of claim 9, the tubular stent defining a longitudinal axis, wherein each directional loop is oriented at a different angle relative to the longitudinal axis so that the distal end portion of the catheter is deflected towards the wall of the venous sinus.

11. The neurovascular venous access system of claim 10, wherein
a plane of the first loop is parallel to a plane of the proximal end opening of the tubular stent,
a plane of the second loop located distally of the first loop is at an angle relative to the longitudinal axis of the tubular stent, and a plane of the third loop located distally of the second loop is perpendicular to the plane of the first loop and the plane of the proximal end opening of the tubular stent.

12. An extravascular access system, comprising:
a tubular stent configured to be deployed in a body lumen, the tubular stent having
a sidewall defining a lumen, a proximal end opening, and an internal scaffolding disposed in the lumen and comprising one or more internal structural members; and
an elongate access catheter having a distal end portion configured to access the body lumen,
wherein when the tubular stent is deployed in the body lumen, and the distal end portion of the catheter is inserted into the proximal end opening of the tubular stent, the one or more internal structural members of the stent deflect the distal end portion of the catheter towards a wall of the body lumen,
the one or more internal structural members comprising a plurality of wires and a plurality of directional loops, wherein each directional loop of the plurality of directional loops is fixedly coupled to at least one wire of the plurality of wires and respectively angularly oriented to define a pathway and deflect the distal end portion of the catheter towards the wall of the body lumen.

13. An extravascular access system, comprising:
a tubular stent configured to be deployed in a body lumen, the tubular stent having
a sidewall defining a lumen, a proximal end opening, and an internal scaffolding disposed in the lumen and comprising one or more internal structural members; and
an elongate access catheter having a distal end portion configured to access the body lumen,
wherein when the tubular stent is deployed in the body lumen, and the distal end portion of the catheter is inserted into the proximal end opening of the tubular stent, the one or more internal structural members of the stent deflect the distal end portion of the catheter towards a wall of the body lumen,
wherein the tubular stent defines a longitudinal axis, and wherein the one or more internal structural members of the tubular stent deflect the distal end portion of the catheter through an opening in the sidewall of the tubular stent, and
wherein the one or more internal structural members of the tubular stent deflect the distal end portion of the catheter through the sidewall opening of the tubular stent at an angle that is 5° to 20° relative to the longitudinal axis of the tubular stent.

14. An extravascular access system, comprising:
a tubular stent configured to be deployed in a body lumen, the tubular stent having
a sidewall defining a lumen, a proximal end opening, and an internal scaffolding disposed in the lumen and comprising one or more internal structural members; and
an elongate access catheter having a distal end portion configured to access the body lumen,
wherein when the tubular stent is deployed in the body lumen, and the distal end portion of the catheter is inserted into the proximal end opening of the tubular stent, the one or more internal structural members of the stent deflect the distal end portion of the catheter towards a wall of the body lumen,
wherein the tubular stent defines a longitudinal axis, and wherein the one or more internal structural members of the tubular stent deflect the distal end portion of the catheter through an opening in the sidewall of the tubular stent, and
wherein the one or more internal structural members of the tubular stent deflect the distal end portion of the catheter through the sidewall opening of the tubular stent at an angle that is 20° to 45° relative to the longitudinal axis of the tubular stent.

15. An extravascular access system, comprising:
a tubular stent configured to be deployed in a body lumen, the tubular stent having
a sidewall defining a lumen, a proximal end opening, and an internal scaffolding disposed in the lumen and comprising one or more internal structural members; and
an elongate access catheter having a distal end portion configured to access the body lumen,
wherein when the tubular stent is deployed in the body lumen, and the distal end portion of the catheter is inserted into the proximal end opening of the tubular stent, the one or more internal structural members of the stent deflect the distal end portion of the catheter towards a wall of the body lumen,
wherein the tubular stent defines a longitudinal axis, and wherein the one or more internal structural members of the tubular stent deflect the distal end portion of the catheter through an opening in the sidewall of the tubular stent, and
wherein the one or more internal structural members of the tubular stent deflect the distal end portion of the catheter through the sidewall opening of the tubular stent at an angle that is 45° to 90° relative to the longitudinal axis of the tubular stent.

* * * * *